(12) United States Patent
De Coulon et al.

(10) Patent No.: US 8,608,926 B2
(45) Date of Patent: Dec. 17, 2013

(54) AMPEROMETRIC IN-PIPE ELECTROCHEMICAL SENSING PROBE

(75) Inventors: Yves De Coulon, Saint-Blaise (CH); Carine Beriet Herrera, Peseux (CH)

(73) Assignee: Neroxis SA, Neuchatel (CH)

( * ) Notice: Subject to any disclaimer, the term of this patent is extended or adjusted under 35 U.S.C. 154(b) by 780 days.

(21) Appl. No.: 12/274,870

(22) Filed: Nov. 20, 2008

(65) Prior Publication Data

US 2010/0122905 A1 May 20, 2010

(51) Int. Cl.
*G01N 27/333* (2006.01)

(52) U.S. Cl.
USPC .......................................................... 204/416

(58) Field of Classification Search
USPC ............ 204/400, 403.02, 415–419, 422, 433;
205/775, 778.5, 782.5, 786.5–787.5,
205/789–789.5, 793
See application file for complete search history.

(56) References Cited

U.S. PATENT DOCUMENTS

| | | | | |
|---|---|---|---|---|
| 4,547,833 A * | 10/1985 | Sharp | ............................ | 361/716 |
| 5,103,179 A * | 4/1992 | Thomas et al. | ............... | 324/438 |
| 5,219,712 A * | 6/1993 | Evans et al. | .................... | 430/311 |
| 5,246,576 A * | 9/1993 | Leader et al. | .................. | 204/431 |
| 5,627,749 A * | 5/1997 | Waterman et al. | ................ | 702/6 |
| 5,725,747 A | 3/1998 | Pinkowski et al. | | |
| 5,939,399 A | 8/1999 | Vertesy et al. | | |
| 6,740,216 B2 * | 5/2004 | Diakonov et al. | ............. | 204/418 |
| 7,189,314 B1 * | 3/2007 | Pace et al. | ..................... | 204/412 |
| 2002/0177763 A1 * | 11/2002 | Burns et al. | .................... | 600/345 |
| 2005/0121322 A1 * | 6/2005 | Say et al. | .................. | 204/403.1 |
| 2007/0098600 A1 * | 5/2007 | Kayyem | ....................... | 422/102 |
| 2009/0105605 A1 * | 4/2009 | Abreu | .......................... | 600/549 |

* cited by examiner

*Primary Examiner* — Susan D Leong
(74) *Attorney, Agent, or Firm* — Young & Thompson (57) ABSTRACT

A sensing probe intended to measure the content of an oxygen reducible substance in a fluid, includes:
- a probe body containing an interface and processing circuit,
- a dry sensing head including an amperometric sensor intended to measure the content of the oxygen reducible substance. The sensing head is removable. The sensing head and the probe body include respectively coupling elements cooperating with each other and able to be separated, and the sensing probe furthermore includes connecting elements designed to connect the removable sensing head to the interface and processing circuit of the probe body.

20 Claims, 8 Drawing Sheets

AMPEROMETRIC IN-PIPE ELECTROCHEMICAL SENSING PROBE

BACKGROUND OF THE INVENTION

The present invention relates generally to the field of electrochemical sensors, particularly to the field of amperometric sensor devices which are intended to detect or measure the content of an oxygen reducible substance in a fluid, and more particularly the amount of chlorine in a fluid.

BACKGROUND OF THE INVENTION

Chlorine sensors are well known in the art.

A first type of chlorine sensor, disclosed for example in U.S. Pat. No. 5,725,747, uses a reagent liquid in which some metallic electrodes are immersed. The first drawback of this type of chlorine sensor is that, due to the presence of a reagent liquid that could contaminate the fluid whose chlorine amount is to measure, they are not suitable when the fluid is drinking water. Additionally, the fluid can dilute the reagent, reducing the lifetime without maintenance. Moreover, they require a periodical maintenance, during which the reagent liquid shall be changed. This maintenance operation has to be performed every two months and has to be made by a technical specialist, since complex operations shall be performed and since the sensor shall be recalibrated. This results in high operating costs.

The document U.S. Pat. No. 5,939,399 discloses an amperometric electrochemical sensor that does not use any reagent liquid. It comprises a semi-conductor sensing element, a measuring circuit and housing. The semi-conductor sensing element has a planar structure and comprises an insulating substrate, a set of planar complete electrodes (one working electrode, one counter electrode and one reference electrode), a diffusion membrane, which is deposited on the working electrode, and connections means to connect the electrodes to the measuring circuit. The semi-conductor sensing element is micro fabricated, being obtained by photolithographic techniques.

At least the semi-conductor sensing element is immersed in a fluid, for example in a pipe. The sensing element constitutes an electrochemical microcell, the electrochemical reaction with the fluid producing an electrochemical current, depending on the amount of chlorine in the fluid.

This type of chlorine sensors has good performances and is also suitable to be used in drinking water, but its constitution is such that the sensing element shall be replaced periodically, approximately once a year. This time limitation is mainly due to the delaminating of the diffusion membrane due to bad adhesion on the working electrode, as well as insufficient packaging, allowing the fluid to penetrate within the probe, creating short-circuit. Compared to a sensor using reagent liquid, the operating costs due to maintenance are reduced, since it occurs less frequently, and since the operation can be performed by a non-qualified person. However, as it is not possible to disassemble the sensor, when the sensing element replacement has to be performed, the whole sensor shall be replaced, i.e. the sensing element, the measuring circuit and the housing. Operating costs remain high.

In addition, the sensing element is placed on a support plate, and this support plate is oriented vertically with respect to the fluid stream. This orientation can be disadvantageous since the fluid could contain some small air bubbles. With a vertical orientation of the plate, it is possible that some air bubbles stay hanged on the sensing element, leading to a mismeasurement since the sensing element is no more in contact with the fluid.

Additionally, the support plate is prominent. This disposition has different drawbacks. The first drawback is that, if some small objects or particles circulate in the fluid, they could damage or even destroy the sensing element if they hit it. The second drawback is that the strain on the plate can be high, in particular when the flow of the fluid is high. The third drawback is that the sensing module is somehow fragile when handling it, the sensing element being directly exposed. The fourth is the limited lifetime of the membrane adhesion leading to bad definition of diffusion layer and change in the sensitivity.

The present invention proposes an electrochemical sensing probe such that these drawbacks are avoided.

SUMMARY OF THE INVENTION

The present invention discloses a sensing probe, intended to measure the content of an oxygen reducible substance in a fluid, comprising
- a probe body containing an interface and processing circuit,
- a dry sensing head comprising an amperometric sensor intended to measure the content of said oxygen reducible substance, wherein said sensing head is a removable sensing head, said sensing head and said probe body comprising respectively coupling means cooperating with each other and able to be separated, and wherein said sensing probe furthermore comprises connecting elements designed to connect said removable sensing head to the interface and processing circuit of said probe body.

In another embodiment, said probe body may comprise a male threaded portion and said removable sensing head may comprise a female threaded portion that cooperates with said male threaded portion of said probe body.

The sensing probe may furthermore comprise sealing means between the probe body and the removable sensing head.

Additionally, the removable sensing head may furthermore comprise a PCB, said PCB being mounted oriented transversally with respect to said sensing probe, the amperometric sensor being mounted on the PCB, on the face opposed to the probe body.

The sensing probe may also furthermore comprise a non-volatile memory and an interface integrated circuit, said non-volatile memory and interface integrated circuit being mounted on said PCB, and said non-volatile memory storing calibration data of said amperometric sensor.

The PCB may furthermore comprise metalized concentric circular traces, said metalized concentric traces being engraved on the side opposed to the amperometric sensor and being electrically connected to said amperometric sensor and said non-volatile memory.

In another embodiment, some protective resin is casted onto the whole surface of the PCB on which the amperometric sensor is mounted, except the surface taken by said amperometric sensor.

In another embodiment, the removable sensing head may furthermore comprise lateral protecting tabs, said tabs being disposed on the periphery of the removable sensing head, and oriented vertically with respect to said PCB.

In another preferred embodiment, the amperometric sensor is a micro fabricated silicon amperometric sensor.

The amperometric sensor may comprise a working electrode, a counter electrode and a reference electrode, said electrodes being planar and micro structured.

The working electrode or the working electrode and the counter electrode may be covered by a selective membrane and said selective membrane being covered partially or totally by a packaging membrane.

In another embodiment, the interface and processing circuit may furthermore comprise a wireless communication circuit, and the probe body may furthermore comprise a battery.

Finally, the removable sensing head may furthermore comprise a battery, and the connecting elements may be replaced by a short range radio interface.

BRIEF DESCRIPTION OF THE DRAWINGS

The above and other objects, features and advantages of the present invention will become further apparent from the following description of the preferred embodiment taken in conjunction with the accompanying drawings, in which.

DETAILED DESCRIPTION

Figure 1:
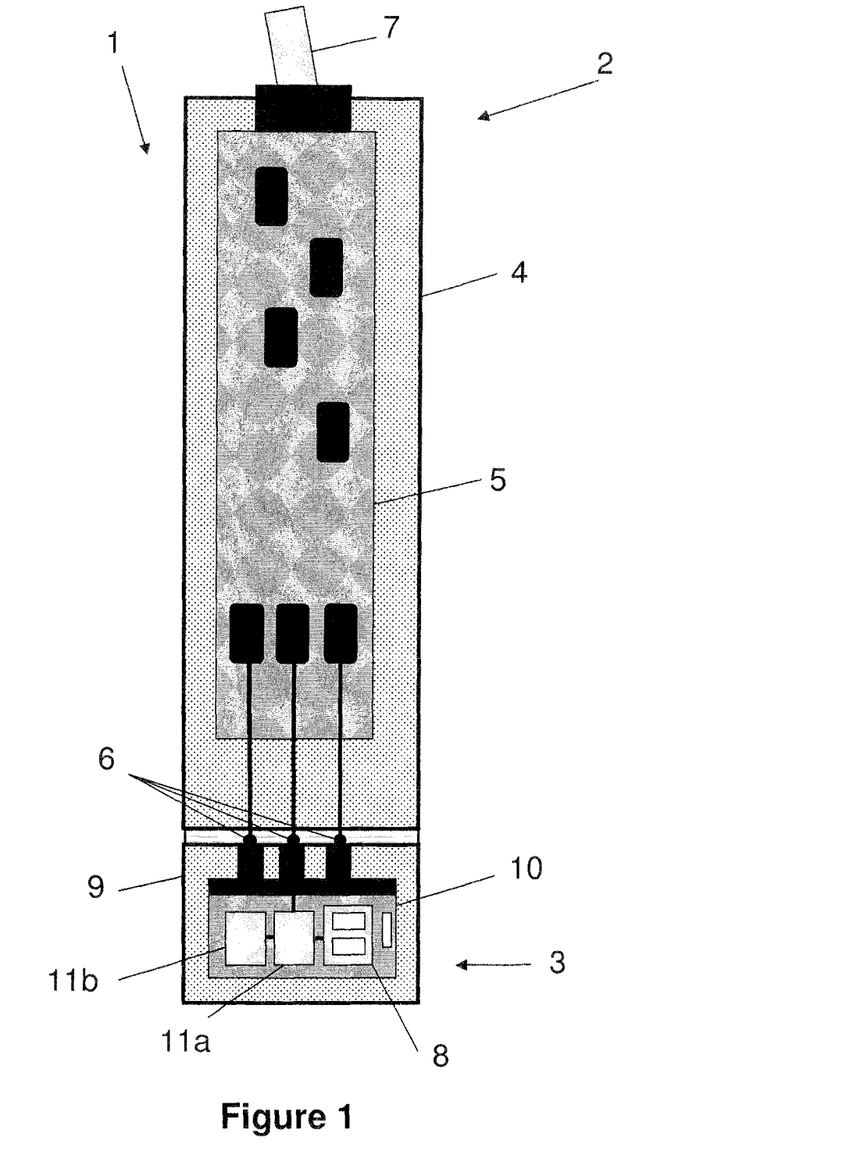
FIG. 1 depicts a schematic view of an electrochemical sensing probe according to the present invention.

FIG. 1 depicts one preferred embodiment of an amperometric electrochemical sensing probe used as a chlorine sensor. Said sensing probe comprises:
 a probe body 2, and
 a removable dry sensing head 3.
The probe body 2 comprises:
 a housing 4,
 an interface and processing circuit 5, comprising for example an interface amplification electronic circuit and a data processing electronic circuit such as a microcontroller, and
 a plurality of connecting elements 6. In this embodiment, the connecting elements are contact tips.

An electrical cable 7 is mechanically linked to the probe body 2 and electrically connected to the interface and processing circuit 5. It is used to provide power supply to the interface and processing circuit 5 and to output some signals of said interface and processing circuit 5.

The removable sensing head 3 comprises a cap 9, a PCB (Printed Circuit Board) 10, a micro fabricated amperometric silicon chlorine sensor 8, an interface integrated circuit (IC) 11a, to transform the sensor current signal into a voltage signal and amplify it, and a non-volatile memory 11b, such as an EEPROM or a flash memory. Obviously, the sensor can be adapted to any oxygen reducible substances to be measured by changing the electrical parameters of the sensing probe. The PCB 10 comprises contact surfaces electrically bounded to the silicon chlorine sensor 8, to the interface IC 11a and to the non-volatile memory 11b, said contact surfaces cooperating with the connecting elements 6 of the probe body. The PCB 10 is fixed or molded into the cap 9, and the silicon chlorine sensor 8, the interface IC 11a and the non-volatile memory 11b are mounted onto the PCB 10, on the face opposed to the module body. A hole is made into the cap 9 in correspondence to the silicon chlorine sensor, so that, when the sensing head is immersed into a fluid, the silicon chlorine sensor electrodes are in contact with the fluid, as will be described below. The silicon chlorine sensor 8 is for example based on a Clark-type cell with working, counter and reference electrodes and a specific photo polymerized membrane deposited at least on the working electrode. Such cell is known in the art and for a comprehensive description, one can refer to the patent application U.S. Pat. No. 5,939,399. The reference electrode can be for example the electrode disclosed in patent application CH 683 874 or can be realized by gluing an Ag—AgCl metal block onto the micro machined silicon chip described hereunder.

Another embodiment of the silicon chlorine sensor will be described hereafter, related with FIG. 6.

For example, the silicon chlorine sensor 8 provides a current proportional to the amount of chlorine in a fluid in which the silicon chlorine sensor 8 is immersed, then the interface IC 11a converts said current into a voltage signal, using a known potentiostatic electronic circuit, and capable to be transmitted to the probe body through the connecting elements 6, in order to be processed by the interface and processing circuit 5 and sent outside the sensing probe. The data stored into the non-volatile memory 11b are also transmitted to the interface and processing circuit 5 using the connecting elements 6.

As the silicon chlorine sensor 8 shall be periodically replaced and thanks to the present invention, only the removable sensing head 3, comprising the silicon chlorine sensor 8, can be replaced. The probe body 2 comprising the interface and processing circuit 5 does not need to be replaced and consequently, the operating costs of the sensor module are substantially reduced compared to the known sensors. Moreover, this replacement requires only a new removable sensing head, but no special liquids or fragile mechanical membranes.

The interface and processing circuit 5 can also comprise means for converting the signal representing the amount of the oxygen reducible substance into a digital data. In that case, the digital data can advantageously be outputted of the interface circuit using any known serial protocol (such as RS232). Digital processing means, such as a microcontroller can also be provided within the interface and processing circuit of the probe body, in order to perform more complex signal processing.

The sensor of the present invention generally gives better performances when a calibration is performed. Therefore, all removable sensing heads 3 are calibrated during fabrication and the calibration data, for example zero and sensitivity, are directly stored into the non-volatile memory 11b of the removable sensing head using known techniques. When a removable sensing head 3 is replaced, the probe body 2 and more precisely the interface and processing circuit 5 can adapt automatically the new removable sensing head without the need of manual calibration nor an intervention of a specialist to recalibrate the sensing probe, by reading in the non-volatile memory 11b the calibration data stored for this replaced removable sensing head 3. The replacement can be done in field by the user.

A calibration is only performed to know the behavior of the sensing module when measuring a known amount of said oxygen reducible substance in fabrication. The data from the calibration procedure are subsequently used to correct the measure made by the sensing module, giving a better measurement precision. Apart from the sensitivity and the zero, the calibration data can consist in a look-up table giving corrected values for a set of measure of the sensing probe.

Figure 2:
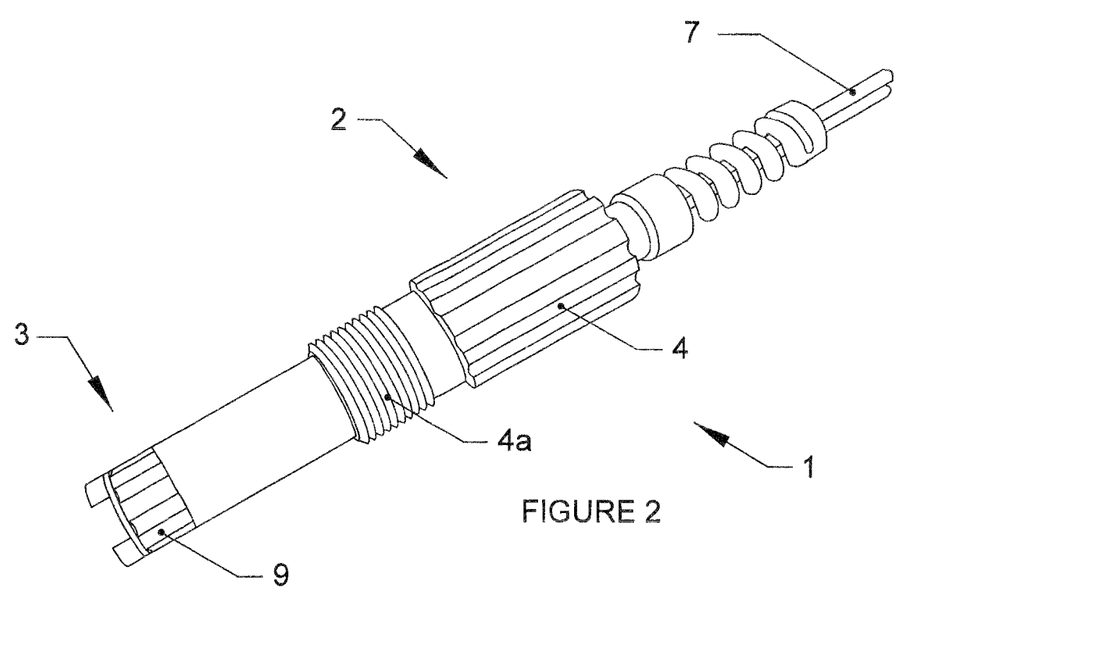
FIG. 2 presents a picture of the sensing probe.

The FIG. 2 shows a picture of a sensing probe, where the removable sensing head 3 is assembled to the probe body 2. Advantageously, the cap 9 and the housing 4 are made in PVC (Polyvinyl Chloride) or using known plastic injection techniques.

Figure 3:
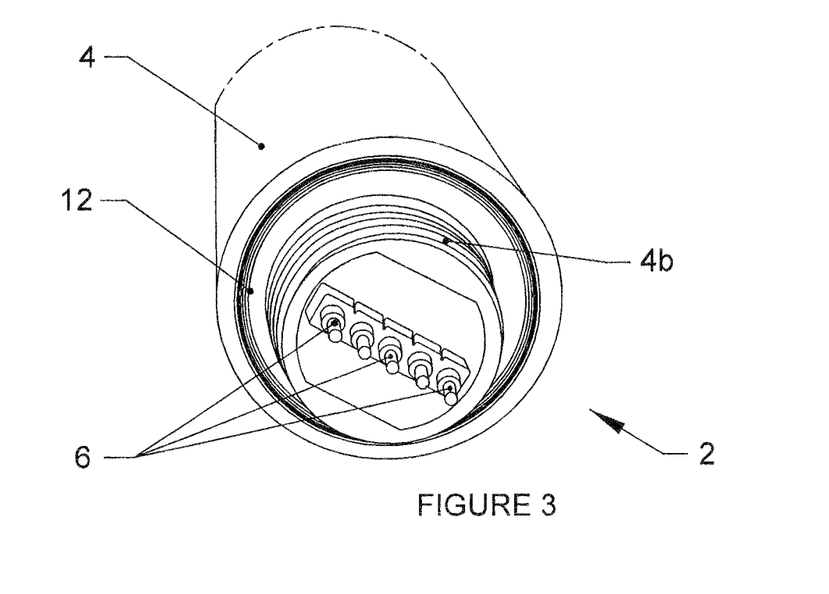
FIG. 3 presents a detailed view of one end of a sensing probe body.

Still referring to the FIG. 2, the housing 4 comprises a first male threaded portion 4a, so that the sensing probe can be screwed into a pipe on which a threaded hole is made. A seal, not shown on the picture allows a good tightness so that no fluid leak of the pipe when a sensing module is mounted, The FIG. 3 presents a detailed view of the end of the probe body 2. The housing 4 comprises, at one end, a second male threaded portion 4b.

Figure 4A:
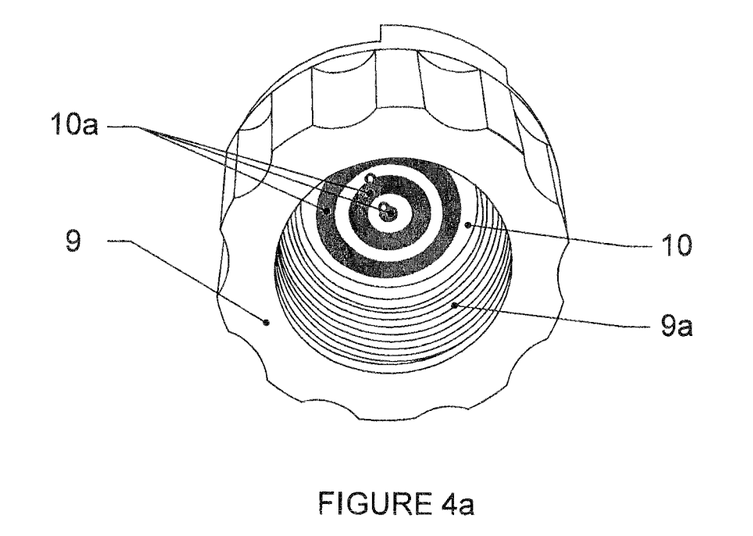
FIGS. 4a and 4b present a detailed front and back view of a removable sensing head.
Figure 4B:
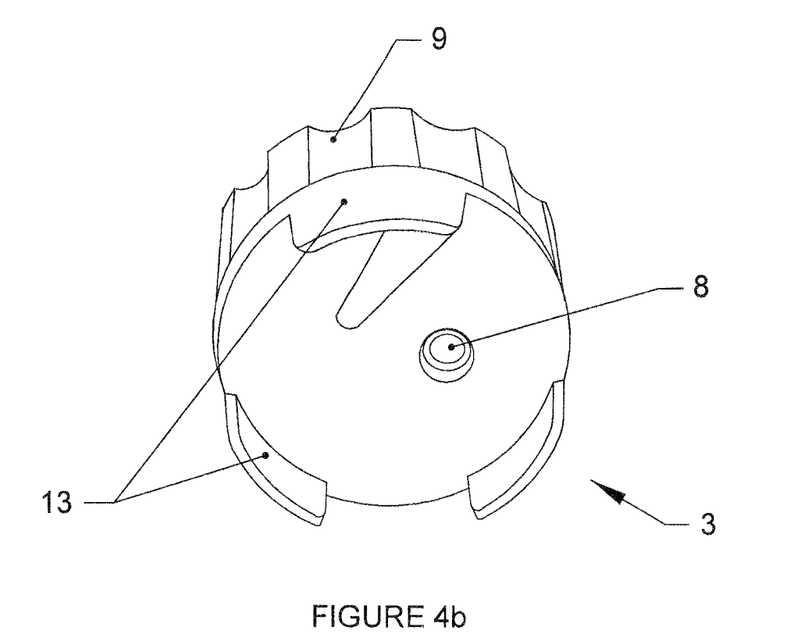

The FIG. 4a presents a detailed back view of the removable sensing head 3, FIG. 4b presenting a detailed front view of the same removable sensing head 3.

The inside of the cap 9 comprises a female threaded portion 9a, this female threaded portion 9a being intended to cooperate with the second male threaded portion 4b of the housing 4, in order to assemble the removable sensing head to the probe body 2. A seal 12 is used to ensure the tightness of the assembly, in particular to ensure that no fluid gets into the removable sensing head 3 or into the probe body 2.

As shown on FIG. 4a, the contact surfaces advantageously consist in a plurality of metalized concentric circular traces 10a engraved on the PCB 10 on the side opposed to the silicon chlorine sensor 8, and being electrically connected to said silicon chlorine sensor 8, said interface IC 11a and said non-volatile memory 11b. This disposition ensures a good connection between the connecting elements 6 and the traces 10a whatever the angular position of the removable sensing head 3 regarding the probe body 2 is.

Advantageously, and in relation with the FIGS. 2, 3 and 4, the PCB 10 is oriented transversally with respect to the sensing module. This orientation provides different advantages:
- makes the connection with the interface and processing circuit 5 of the probe body 2 very simple, by using the metalized traces 10a and the connecting elements 6,
- makes the deposition of the epoxy encapsulating resin for protecting the sensor, easier,
- reduces the strain on the PCB 10 and the silicon chlorine sensor 8, when submitted to a flow and compared to a vertical orientation,
- reduces the risk that a small object or some particles of the fluid hit and damage the removable sensing head, and
- reduces the probability that some small bubbles stay hanged on the silicon chlorine sensor, since the flow will tend to carry these bubbles away of the silicon chlorine sensor.

The sensing module, according to the invention, can resist to a pressure of up to 10 bars and therefore can be used directly in pressurized pipe up to ten bars, without the need of dedicated low pressure measuring chamber.

Additionally, for a better protection of the sensor 8 when handling the removable sensing head 3, some lateral protecting tabs 13 are disposed vertically with respect to said PCB, on the periphery of the removable sensing head 3 around the sensor 8, as shown on FIG. 4b. These protecting tabs 13 prevent the sensor 8 to be damaged when handled or stored. They can be directly molded with the cap 9.

Figure 5:
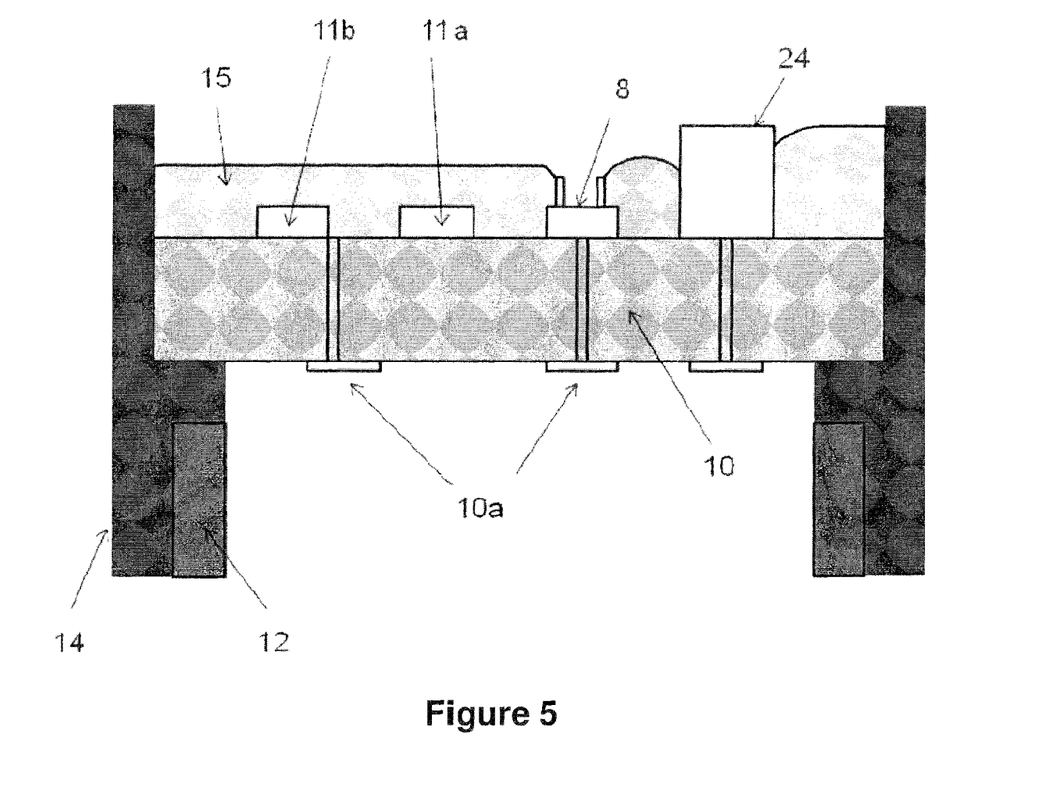
FIG. 5 presents a cross section of another embodiment of the removable sensing head.

In another embodiment of the removable sensing head, referring to FIG. 5, the PCB 10 is disposed into a ring 14. A protective epoxy resin 15 is casted onto the whole surface of the PCB on which the sensor is mounted, except the surface taken by the sensor. The reference electrode of the sensor 8 can be mounted on the PCB 10, as described on FIG. 5, or directly on the silicon sensing chip as described above in FIG. 6.

Figure 6A:
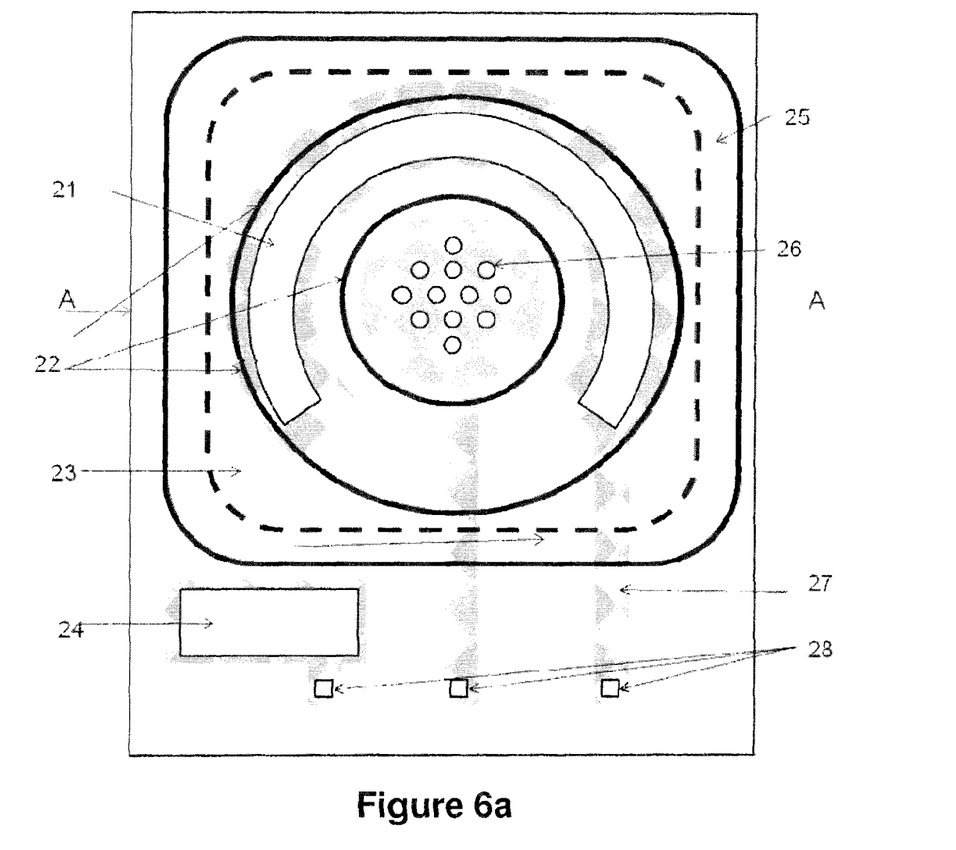
FIGS. 6a-6c present a micro fabricated amperometric silicon chlorine sensor.
Figure 6B:
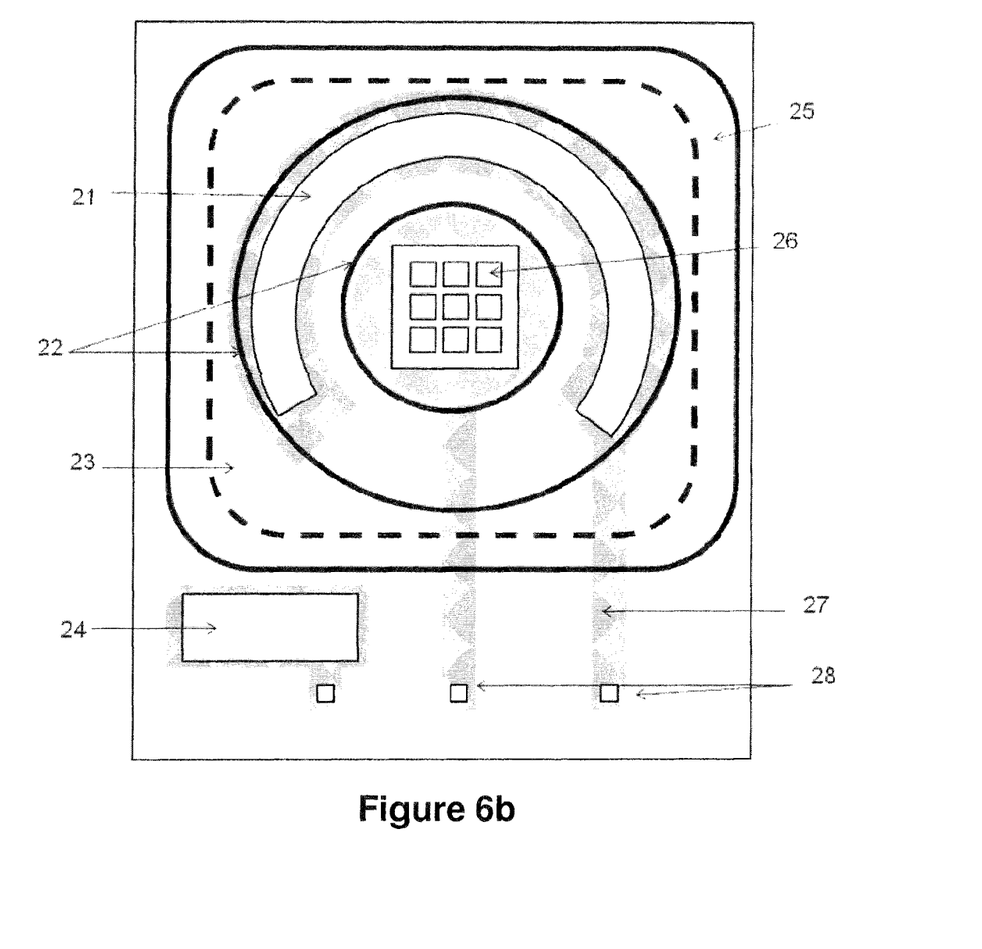
Figure 6C:
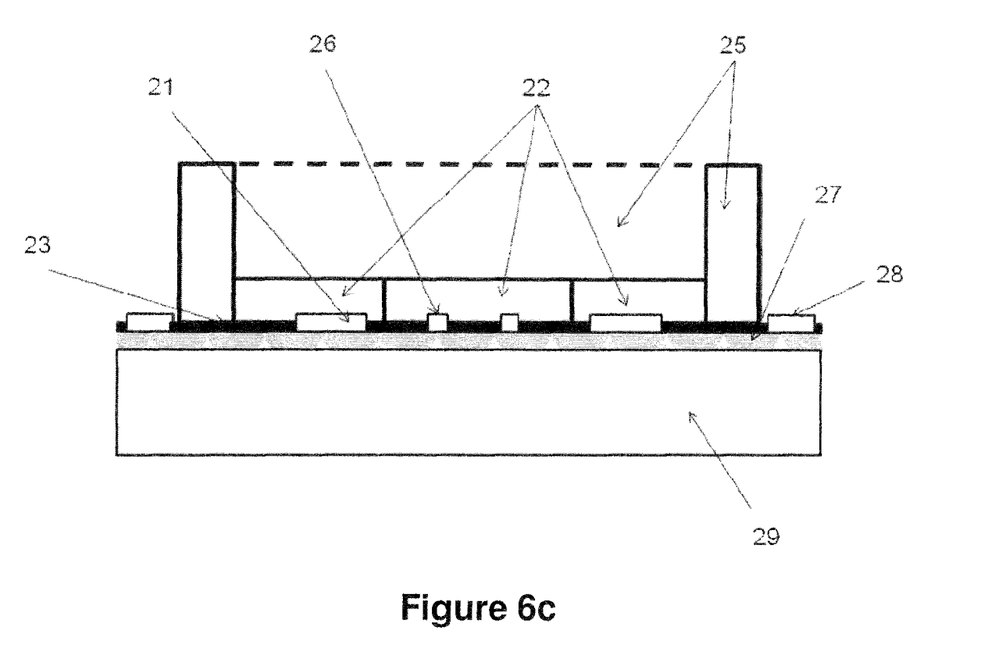

As for the preceding embodiments, the removable sensing head 3 is screw able with the probe body 2 and incorporates a silicon chlorine sensor in the form of a micro machined silicon chip as described in FIGS. 6a, 6b and 6c, with planar electrochemical electrodes in noble metal layers or boron doped diamond (BDD) layer, with covalently bonded planar polymer diffusion layer. A front view is presented in FIGS. 6a and 6b. In the middle of the chip, there are two planar micro structured electrodes the counter electrode 21 and the working electrode 26, both on top of an isolation layer 23. The principle of the measurement remains identical and is based on a Clark-type cell with a working electrode 26, a counter electrode 21 and a reference electrode 24. The key element is the photo-polymerized selective membrane 22 deposited on the silicon chip, either on the working electrode 26 or on the working electrode 26 and counter electrode 21.

The polymer membranes are photo polymerized in planar geometry with large adhesion area with themselves, with passivation layer and with the epoxy resin of the removable sensing head.

This principle of amperometry is based on the measurement of the current between the working electrode and the counter electrode which is induced by a Redox reaction at the working electrode. The reference conditions are chosen in such a way that the current measured at the working electrode 26 is directly proportional to the concentration of Redox active specie in the analyte solution. REDOX species could be chlorine, using HOCl, HOBr or ClO2. The sensor also detects bio-chlorine, or chlorine realized by salt—water electrolysis systems. The electrical potential of the working electrode 26 versus the measured solution is achieved by a separate reference electrode 24 and is controlled by a known potentiostatic electronic system. The working electrode 26 as well as the counter electrode 21 are thin film deposited on the micro machined silicon chip, which includes a passivated conductive layer to easily create the electrical contact towards the PCB. Reference electrode 24 is realized either by a thin layer of Ag—AgCl on the silicon chip, or a metallic flat structure bonded on the chip or simply by a wire bonded to the chip composed of AG—AgCl, realizing a pseudo reference.

The electrodes are micro structured on the isolation layer in such a way to enhance the adhesion of the planar membranes with the oxide of the passivation and the oxide of the metals.

The working electrode 26 and the counter electrode 21 are micro structured in order not to cover the entire isolation layer, leading to let a certain amount of isolation surface in contact with the planar selective membrane 22. The planar selective membrane 22 can be a polyhema polymer membrane. This micro structuration can be round, as in FIG. 6a or square, as in FIG. 6b. So, the selective membrane 22, on the top of these electrodes, is covalently bonded to the oxygen of the isolation layer or to the oxygen of the oxidized metal planar electrodes. By choosing appropriately the proportion of metal electrodes layer or the proportion of isolation layer, typically 50% and 50%, depending on the metal nature of the electrodes such as Platinum, Gold, Tantalum, titanium, the adhesion of diffusion membrane can be maximized.

Compared to standard electrochemical cell with chemical reagent, the signal to noise ratio is here enhanced due to the miniature size of the electrochemical cell and the well defined, by the selective membrane, of the diffusion layer.

The membrane 22, for example polyhema with good proportion of monomers, is designed in order to cover the planar working electrode 26 as well as the planar counter electrode 21. These electrodes are micro structured in order to increase the membrane adhesion to the isolation layer underneath, as well as to facilitate the adhesion between both membranes. This planar membrane can cover, by design, the working electrode 26 as well as the counter electrode 21. Moreover, in order to enhance the adhesion, the membrane 22 is adjacent to the packaging membrane 25.

The number of dots or squares of the membrane depends on the metals realizing the electrodes as well as of the type of passivation layer, silicon oxide or silicon nitride. The reference electrode 24 is, for example, mounted on a special contact on the silicon chip.

The packaging membrane 25, for example polysiloxane, surrounds the working electrode 26 as well as the counter electrode 21, and is connected to the epoxy resin of the encapsulation as well as to the selective membrane 22, in order to avoid any packaging leaks. The packaging membrane 25 can cover partially or totally the diffusion membrane 22 in order to enhance the lifetime of the diffusion membrane and to select different electrochemical species.

All the noble metals electrodes as well as the reference electrodes are connected to an open electrical contact 28 by a conductor layer 27, covered and protected by the passivation layer, except under the electrodes. This conductor layer 27 assures a good electrical contact between the electrodes and the electrical contact. The FIG. 7c presents a side view of the micro machined amperometric silicon chip, where the adhesion region between the selective membrane 22, which covers by design the working electrode 26 or the working electrode 26 and the counter electrode 21, can be covalently bonded to the isolation layer 23 between the metal electrode dots of the working electrode 26.

The packaging membrane 25 has a thickness 3-5 times higher than the diffusion membrane 22 in order to be glued easily with the epoxy resin covering the removable sensing head, as described in FIG. 5.

The geometry definition of the planar membranes increases the quality of packaging, and consequently the lifetime of the sensing probe.

Figure 7:
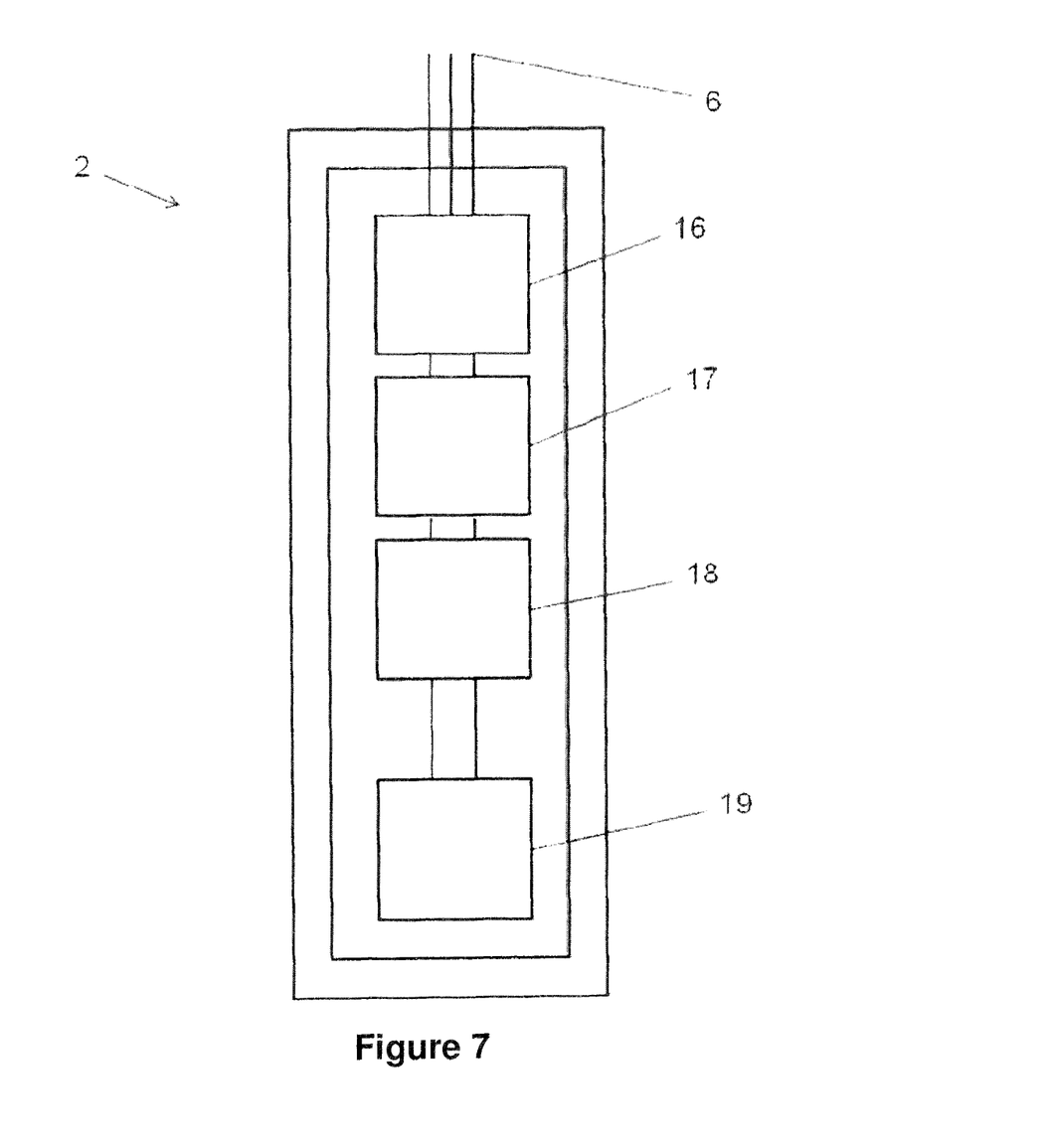
FIG. 7 depicts a schematic view of the probe body.

In another embodiment of the sensor body 2 in reference to FIG. 7, the interface and processing circuit 5 comprises an interface circuit 16, a processing circuit 17 (such as a microcontroller), and a wireless communication circuit 18, in order to transmit the signal representing the amount of the oxygen reducible substance outside the probe body 2. Additionally, the probe body 2 comprises a battery 19, providing the interface and processing circuit 5 with power. This solution is very convenient since no cable is necessary to connect the sensing probe.

The sensing probe of the invention needs neither reagents, nor maintenance or calibration during one year. It is easy to handle, plug and play. It has no risk of chemical reactant losses.

The preceding description is provided as non-limiting examples and one skilled in the art will not encounter any particular difficulties in implementing some variations of embodiment without going outside the scope of the present invention.

For example, the assembly between the removable sensing head 3 and the probe body 2 could be made through any adapted coupling means cooperating with each other and able to be separated, for example a bayonet assembly or through a clipping assembly, using known techniques. The module body could also be made in metal instead of PVC.

It is also possible to remove all the electrical connections between the removable sensing head and the probe body, by embedding a short range radio IC into the removable sensing head and into the probe body, as well as a small battery into the removable sensing head. This solution avoids any electrical contact problems and makes the tightness of the sensing probe easier.

Additionally, the system can also be used to measure other type of substance in a fluid, by changing the silicon chlorine sensor for another type of sensor.

The invention claimed is:

1. A sensing probe, configured to measure the content of an oxygen reducible substance in a fluid, comprising:
   a probe body containing an interface and processing circuit,
   a dry sensing head comprising an amperometric sensor configured to measure the content of said oxygen reducible substance,
   wherein said dry sensing head is removable from said probe body, said dry sensing head and said probe body comprising respective coupling means cooperating with each other and configured to be separable to allow removing of said dry sensing head from said probe body,
   wherein said sensing probe further comprises connecting elements configured to connect in a removable manner said removable dry sensing head to the interface and processing circuit of said probe body, and
   wherein the removable dry sensing head further comprises a cap and a printed circuit board (PCB) fixedly attached to the cap, said printed circuit board (PCB) being mounted transversally with respect to said sensing probe, the amperometric sensor being mounted on the printed circuit board (PCB), on a face opposed to the probe body.

2. The sensing probe according to claim 1, wherein said coupling means of said probe body comprises a male threaded portion and wherein said coupling means of said removable dry sensing head comprises a female threaded portion that cooperates with said male threaded portion of said probe body.

3. The sensing probe according to claim 2, wherein it furthermore comprises sealing means between the probe body and the removable dry sensing head.

4. The sensing probe according to claim 1, further comprising a non-volatile memory and an interface integrated circuit, said non-volatile memory and interface integrated circuit being mounted on said printed circuit board (PCB), and wherein said non-volatile memory stores calibration data of said amperometric sensor.

5. The sensing probe according to claim 4, wherein said printed circuit board (PCB) furthermore comprises metalized concentric circular traces, said metalized concentric traces being engraved on the side opposed to the amperometric sensor and being electrically connected to said amperometric sensor and said non-volatile memory.

6. The sensing probe according to claim 1, wherein a protective resin is casted onto the whole surface of the printed circuit board (PCB) on which the amperometric sensor is mounted, except the surface taken by said amperometric sensor.

7. The sensing probe according to claim 1 wherein said removable dry sensing head furthermore comprises lateral protecting tabs, said tabs being disposed on the periphery of the removable dry sensing head, and oriented vertically with respect to said printed circuit board (PCB).

8. The sensing probe according to claim 1, wherein said amperometric sensor is a micro fabricated silicon amperometric sensor.

9. The sensing probe according to claim 1, wherein said amperometric sensor comprises a working electrode, a counter electrode and a reference electrode, said electrodes being planar and micro structured.

10. The sensing probe according to claim 9, wherein the working electrode is covered by a selective membrane and wherein the selective membrane is covered partially or totally by a packaging membrane.

11. The sensing probe according to claim 9, wherein the working electrode and the counter electrode are covered by a selective membrane and wherein the selective membrane is covered partially or totally by a packaging membrane.

12. The sensing probe according to claim 1 wherein said interface and processing circuit furthermore comprises a wireless communication circuit, and wherein the probe body furthermore comprises a battery.

13. A sensing probe, configured to measure the content of an oxygen reducible substance in a fluid, comprising
   a probe body containing a short range radio interface and processing circuit,
   a dry sensing head comprising an amperometric sensor configured to measure the content of said oxygen reducible substance,
   wherein, said dry sensing head is a removable dry sensing head, said dry sensing head and said probe body comprising respective coupling means cooperating with each other and configured to be separable to allow removal of said dry sensing head from said probe body, and
   wherein said sensing probe further comprises a short range radio interface enabling wireless communication between said removable dry sensing head and the radio interface and processing circuit of said probe body.

14. The sensing probe of claim 13, wherein, the removable dry sensing head further comprises a cap and a printed circuit board (PCB) fixedly attached to the cap.

15. A sensing probe, configured to measure the content of an oxygen reducible substance in a fluid, said sensing probe comprising:
   a dry sensing head; and
   a probe body, the probe body comprising i) a housing, and ii) an interface and processing circuit located within the housing, wherein,
   the sensing head comprises a cap, a printed circuit board fixed into the cap, an amperometric silicon sensor mounted on the printed circuit board, an interface integrated circuit mounted on the printed circuit board and transforming a sensor current signal from the sensor into a voltage signal,
   the cap comprises a hole in correspondence to the silicon sensor, so that, when the sensing head is immersed into a fluid, electrodes of the silicon sensor are in contact with the fluid, and
   each of the cap of the dry sensing head and the probe body comprise leak-tight complementary coupling elements providing for removal of the cap from the probe body.

16. The sensing probe of claim 15, wherein,
   the probe body further comprises a plurality of connecting elements located at a first distal end of the probe body,
   the sensing head further contact surfaces electrically bounded to the sensor and to the interface integrated circuit, the contact surfaces of the dry sensing head being plural concentric metalized traces, and
   when the cap of the dry sensing head is mounted to the probe body, the connecting elements of the probe body make a connection with contact surfaces of the dry sensing head.

17. The sensing probe of claim 15, further comprising:
   an electrical cable mechanically linked to the probe body and electrically connected to the interface and processing circuit,
   the electrical cable i) providing power supply input to the interface and processing circuit, and ii) providing signal output from the interface and processing circuit to outside of the probe body.

18. The sensing probe of claim 15, wherein,
   the housing comprises a first male threaded portion with exposed threads allowing the housing to be screwed into another element having a first female threaded portion complementary to the first male threaded portion; and
   the coupling element of the housing comprises a second male threaded portion at a first distal end, wherein,
   the coupling element of the cap comprises a second female threaded portion complementary to the second male threaded portion allowing the cap to be screwed onto the first distal end of the housing in a leak-tight manner.

19. The sensing probe of claim 15, wherein the sensor is a chlorine sensor.

20. The sensing probe of claim 15, wherein,
   the interface and processing circuit of the probe body is a first wireless interface, and
   the dry sensing head further comprises a second wireless interface configured to communicate signals from the sensor to the first wireless interface of the probe body.

* * * * *